(12) United States Patent
Sanphui et al.

(10) Patent No.: US 10,377,712 B2
(45) Date of Patent: Aug. 13, 2019

(54) PROCESS FOR PREPARATION OF APREMILAST AND NOVEL POLYMORPHS THEREOF

(71) Applicant: LUPIN LIMITED, Mumbai (IN)

(72) Inventors: Palash Sanphui, Pune (IN); Ananda Pundlik Sapdhare, Pune (IN); Arunkumar Digambar Patil, Pune (IN); Hemraj Mahadeorao Lande, Pune (IN); Gurvinder Pal Singh, Pune (IN); Puma Chandra Ray, Pune (IN); Nandu Baban Bhise, Pune (IN); Girij Pal Singh, Pune (IN); Mithun Dasharath Surwase, Pune (IN); Shantanu Gokuldas Varade, Pune (IN); Govind Dnyanoba Ausekar, Pune (IN); Radhakrishna Bhikaji Shivdavkar, Pune (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 15/577,102

(22) PCT Filed: May 26, 2016

(86) PCT No.: PCT/IB2016/053083
§ 371 (c)(1),
(2) Date: Nov. 27, 2017

(87) PCT Pub. No.: WO2016/189486
PCT Pub. Date: Dec. 1, 2016

(65) Prior Publication Data
US 2018/0230097 A1    Aug. 16, 2018

(30) Foreign Application Priority Data

May 26, 2015  (IN) .................... 2046/MUM/2015
May 26, 2015  (IN) .................... 2048/MUM/2015

(51) Int. Cl.
C07D 209/48    (2006.01)
C07C 315/04    (2006.01)

(52) U.S. Cl.
CPC .......... *C07D 209/48* (2013.01); *C07C 315/04* (2013.01); *C07B 2200/07* (2013.01)

(58) Field of Classification Search
CPC .................................................. C07D 209/48
See application file for complete search history.

(56) References Cited

U.S. PATENT DOCUMENTS

| 7,427,638 B2 | 9/2008 | Muller et al. |
| 7,893,101 B2 | 2/2011 | Muller et al. |
| 8,242,310 B2 | 8/2012 | Saindane et al. |
| 2013/0217919 A1 | 8/2013 | Connolly et al. |

*Primary Examiner* — Shawquia Jackson
(74) *Attorney, Agent, or Firm* — Duane Morris LLP; Gregory M. Lefkowitz; Jason M. Nolan

(57) ABSTRACT

The present invention provides an improved process for preparation of an intermediate of apremilast. The present invention also provides an improved process for preparation of apremilast. This invention also provides novel polymorphs of apremilast. The present invention also provides pharmaceutical compositions of novel polymorphs of apremilast. This invention also provides a process for preparation of novel polymorphs of apremilast, which are cost-effective, robust, and viable at plant scale.

12 Claims, 18 Drawing Sheets

Crystal data of Form M of apremilast

| Chemical formula | $C_{22}H_{24}N_2O_7S, H_2O$ |
|---|---|
| Formula Weight | 478.52 |
| Temperature (K) | 293(2) |
| Wavelength (Å) | 1.5418 |
| Crystal lattice | monoclinic |
| Space group | $P2_1$ |
| a, b, c [Å] | 16.6797(15)  5.7377(5) 12.0688(11) |
| α, β, γ [°] | 90,  99.186(7), 90 |
| V [Å$^3$] | 1140.21(18) |
| Z | 2 |
| D(calc) [g/cm$^3$] | 1.394 |
| Refined parameters | 180 |
| No. of background points | 25 |
| $R_p$ | 0.0233 |
| $wR_p$ | 0.0316 |
| $R(F^2)$ | 0.0753 |
| $\chi^2$ | 3.663 |

PROCESS FOR PREPARATION OF APREMILAST AND NOVEL POLYMORPHS THEREOF

CROSS-REFERENCE TO RELATED APPLICATIONS

This application is a § 371 national stage entry of International Application No. PCT/IB2016/053083, filed on May 26, 2016, which claims priority to Indian Patent Application No. 2046/MUM/2015, filed on May 26.2.015 and Indian Patent Application No. 2048/MUM/2015, flied on May 26, 2015, the entire contents of which are incorporated herein by reference.

FIELD OF INVENTION

The present invention provides an improved process for preparation of an apremilast. The present invention also provides novel polymorphs of apremilast and processes for their preparation and pharmaceutical compositions for the treatment of psoriatic arthritis.

BACKGROUND OF INVENTION

Tumor necrosis factor alpha (TNFα) is a cytokine produced by monocytes and macrophages. It is found in synovial cells and macrophages in the tissues. It can be produced by many other cell types such as CD4+ lymphocytes, NK cells, neutrophils, mast cells, eosinophils, and neurons.

Apremilast is a TNFα inhibitor and marketed in United States under the brand name OTEZLA®. Apremilast is indicated for the treatment psoriatic arthritis. It is also used to treat moderate to severe plaque psoriasis in certain patients. The chemical structure of apremilast described in compound 1 as below.

Compound 1

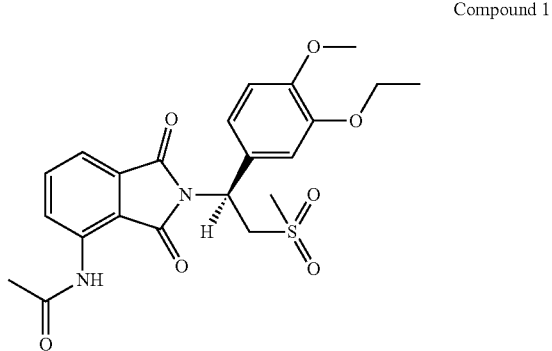

Apremilast is a white to pale yellow powder in appearance. The drug substance is the S-enantiomer of N-[2-[1-(3-ethoxy-4-methoxy-phenyl)-2-(methylsulfonyl) ethyl]-2,3-dihydro-1,3-dioxo-1H-isoindol-4-yl] acetamide.

The U.S. Pat. No. 8,242,310 describes a process for preparation of amine compound of formula (I) by reacting benzonitrile compound of formula (IV) with Lithiumdimethylsulfone compound. The present invention also provides the process for preparation of intermediate of formula A and its conversion to apremilast in subsequent steps.

The U.S. Pat. No. 7,427,638 describes S-enantiomer of apremilast as a product and process for preparation thereof.

The U.S. Pat. Nos. 7,893,101 and 8,093,283 discloses a Form A, Form B, Form C, Form D, Form E, Form F and Form G of apremilast and process for preparation thereof.

SUMMARY OF INVENTION

The invention provides an improved process for preparation of Apremilast.

The present invention also provides novel polymorphs of apremilast and processes for preparation thereof. Particularly, these polymorphs of apremilast are viable and stable at plant scale. Further, present invention provides pharmaceutical compositions comprising apremilast and one or more pharmaceutically acceptable excipients and their use for the treatment of psoriatic arthritis.

In one aspect of the present invention provides crystalline Form M of apremilast, characterized by at least one of the following properties
i) Powder X-Ray diffraction pattern (PXRD) substantially in accordance with FIG. 12;
ii) Powder X-Ray diffraction (PXRD) pattern having peaks at 5.3, 8.4, 13.98, 16.64, 21.46, ±0.2° 2theta values;
iii) thermogravimetric analysis (TGA) substantially in accordance with FIG. 13.
iv) differential scanning calorimetric (DSC) thermogram substantially in accordance with FIG. 14.

In one of the embodiment, the crystalline Form M of apremilast is stable

In another aspect of the present invention provides a process of preparing Form M of apremilast comprising
a) contacting apremilast with at least one solvent;
b) heating the mixture of step a);
c) adding the mixture of step b) to water;
d) cooling the mixture; and e) isolating the crystalline Form M of apremilast.

Another aspect of the present invention provides a crystal of Form M of apremilast and process for preparation thereof.

Another aspect of the present invention provides crystalline Form L of apremilast, characterized by PXRD pattern having peaks at 11.17, 14.0, 16.17, 17.90, and 26.86, ±0.2° 2theta values; or characterized by X-ray diffraction pattern as depicted in FIG. 5.

Another aspect of the present invention provides crystalline Form N of apremilast, characterized by PXRD pattern having peaks at 7.90, 14.64, 17.20, 19.06, and 24.95, ±0.2° 2theta values; or characterized by X-ray diffraction pattern as depicted in FIG. 10.

Another aspect of the present invention provides crystalline Form O of apremilast, characterized by PXRD pattern having peaks at 7.30, 11.16, 17.60, and 26.18, ±0.2° 2theta values; or characterized by X-ray diffraction pattern as depicted in FIG. 11.

Another aspect of the present invention provides pharmaceutical compositions comprising crystalline apremilast Form M or Form O or Form N or Form L and one or more pharmaceutically acceptable excipients.

In another aspect of the present invention provides the use of these polymorphs for the treatment of psoriatic arthritis.

OBJECT OF THE INVENTION

The object of this invention is to provide an improved process for preparation of racemic amine of compound of formula (A), which is an intermediate of apremilast.

In another object of the present invention is to provide an improved process for preparation of apremilast from racemic amine compound of formula (A).

In another object of the present invention is to provide a novel process for preparation apremilast through green, eco-friendly, feasible and cost-effective method.

In another object of the present invention is to provide novel polymorphs of apremilast which are more stable, cost-effective, and viable at plant scale.

DETAILED DESCRIPTION

Figure 1:
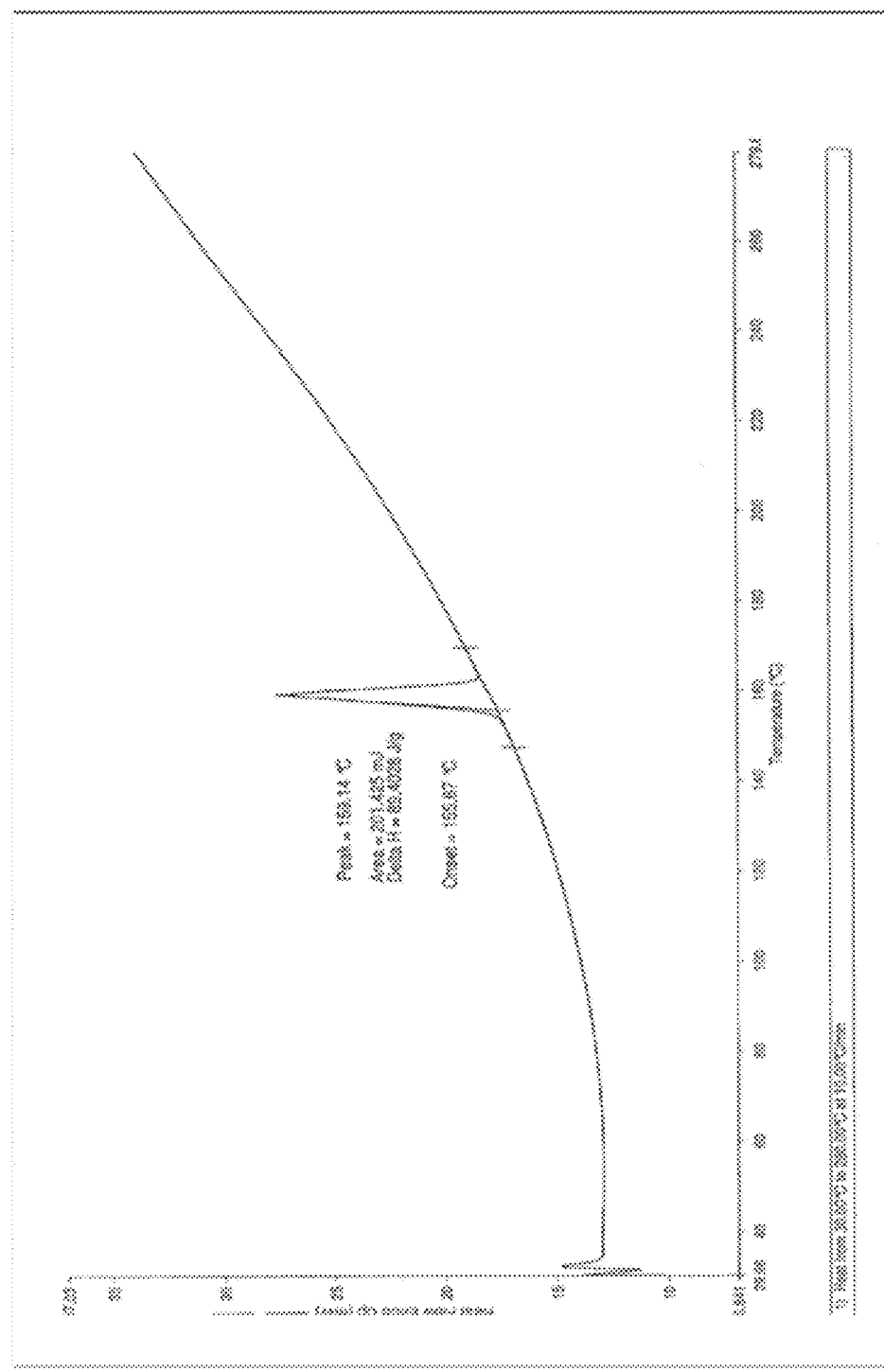
FIG. 1 depicts Differential Scanning calorimetry (DSC) of apremilast.
Figure 2:
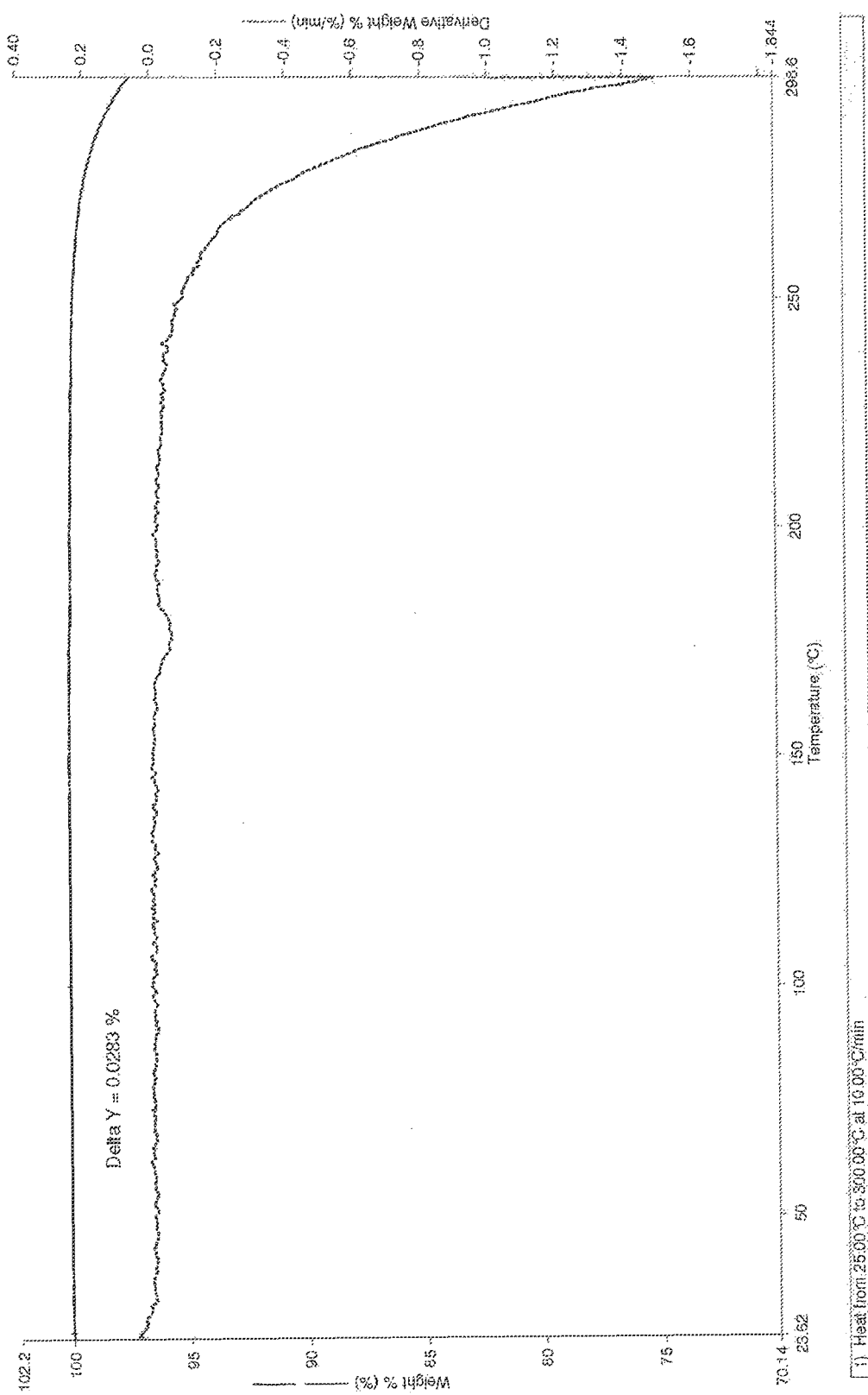
FIG. 2 depicts Thermal Gravimetric Analysis (TGA) of apremilast.
Figure 3:
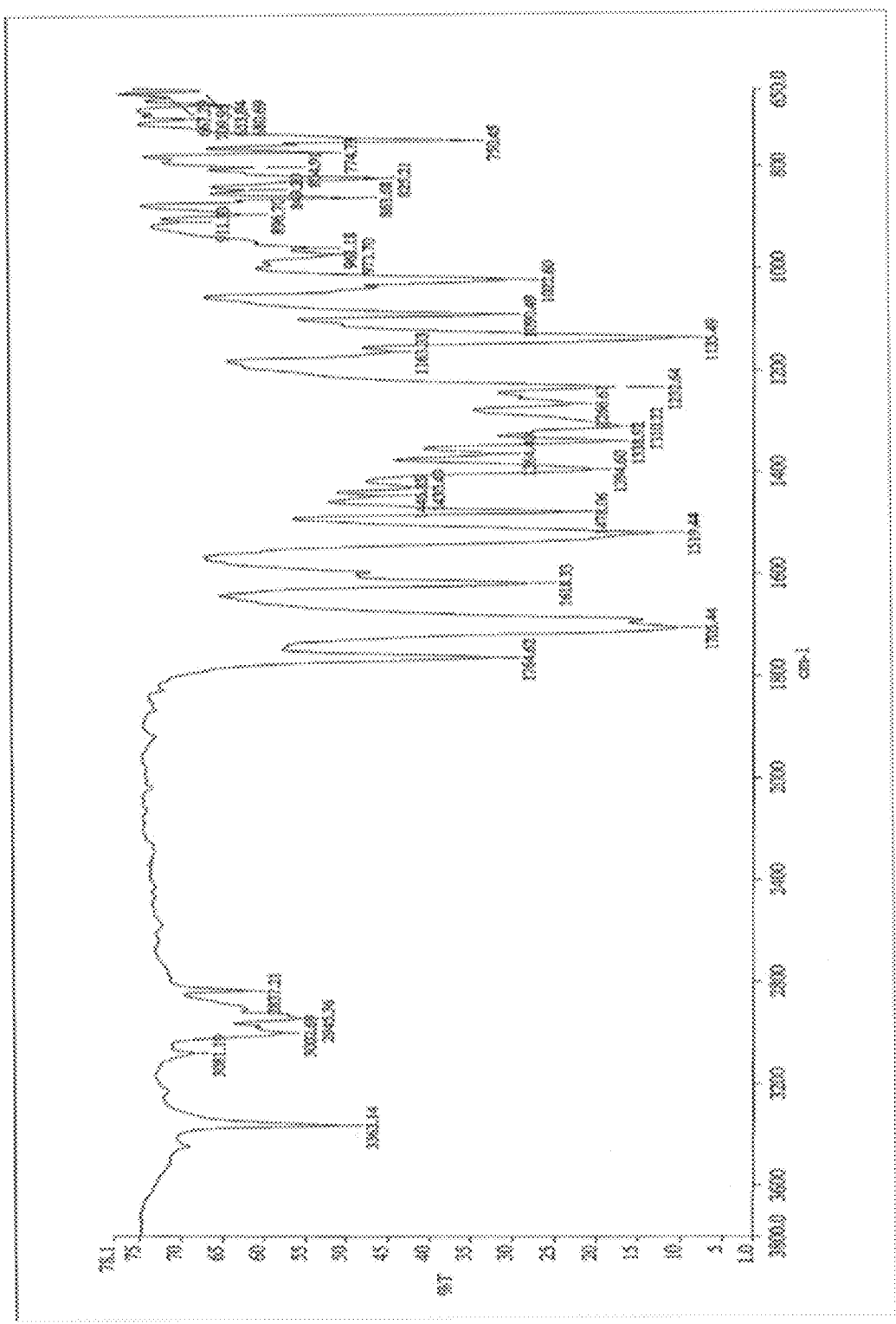
FIG. 3 depicts Infra-red Spectroscopy (IR) of apremilast.
Figure 4:
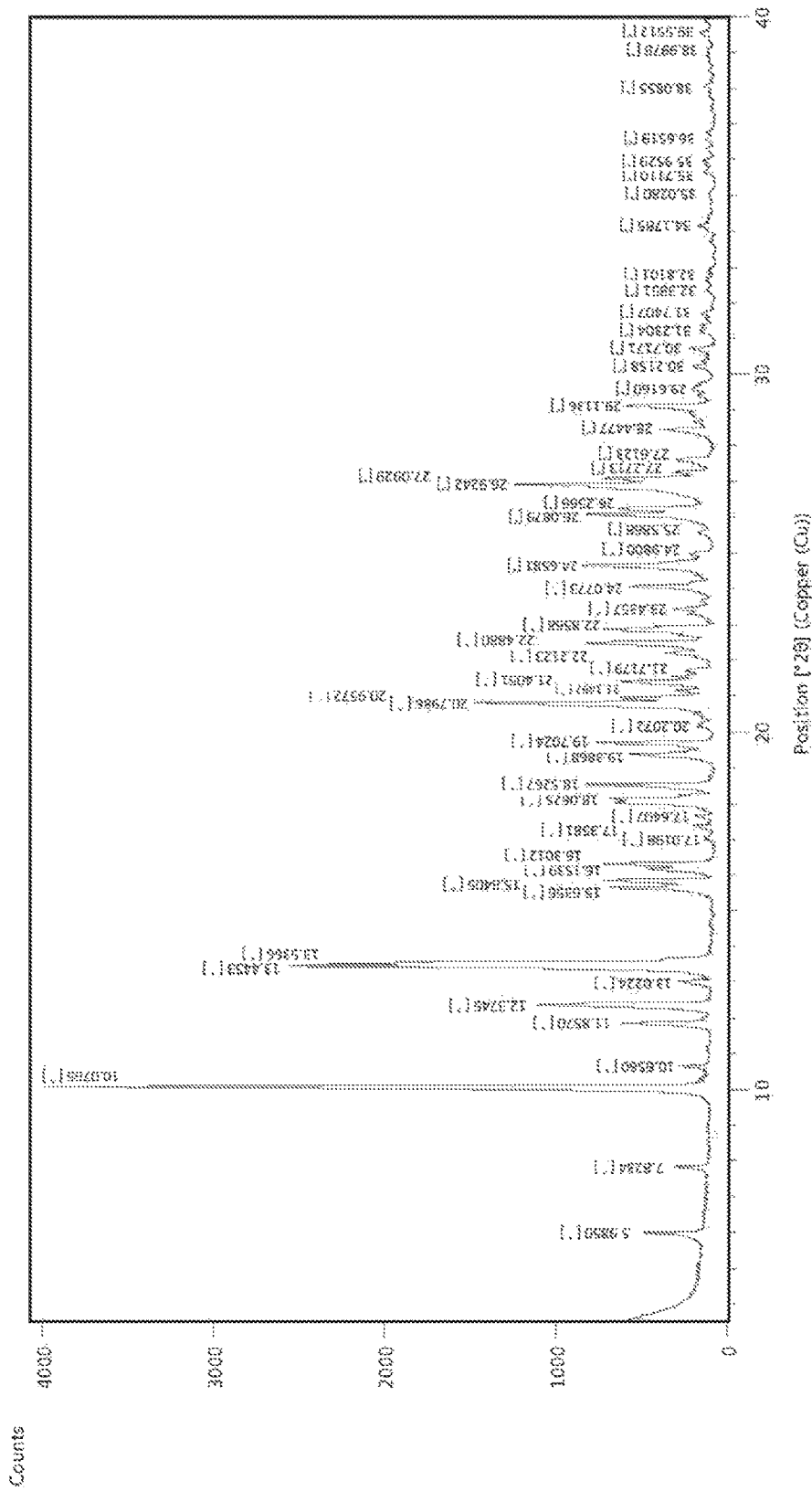
FIG. 4 depicts X-ray Powder Diffraction (XRPD) of apremilast.

The present invention provides an improved process for preparation of apremilast via intermediate of formula A and its process. This intermediate is prepared by using cheap, cost effective and non-hazardous reagents. The present invention provides an improved process for preparation of apremilast (compound C) as below in reaction scheme 1.

Reaction Scheme I

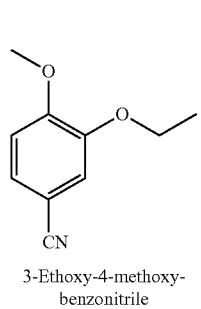

3-Ethoxy-4-methoxy-benzonitrile

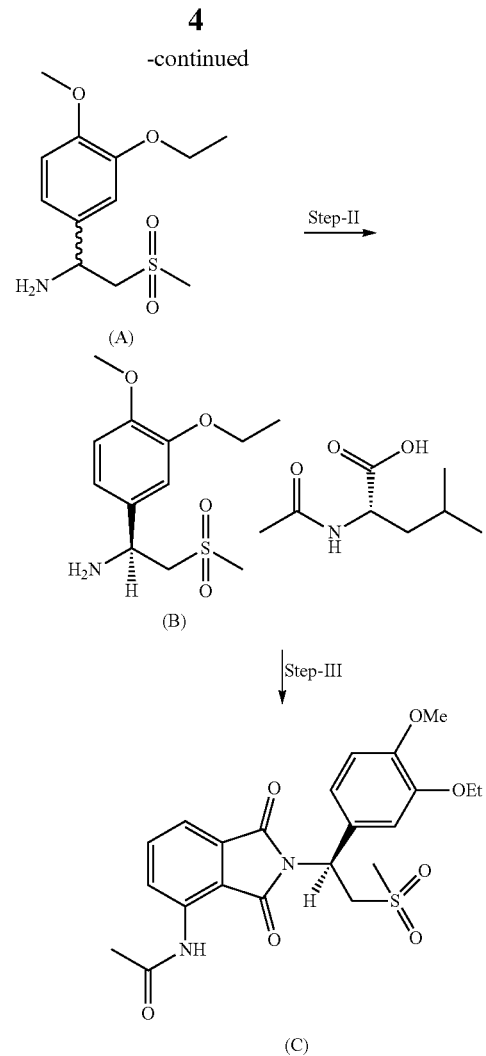

One of the aspects of this invention is to provide a process for preparing compound of formula (A) i.e. racemic amine in step-1 in which 3-ethoxy-4-methoxybenzonitrile is reacted with dimethyl sulfone and a base in an organic solvent. The reaction mass is treated with a reducing agent to give racemic amine compound of formula (A). The base used is in organic or organic base known in the art. The base includes, but not limited to sodium hydride, sodium hydroxide, potassium hydroxide, potassium-HMDS, sodium-HMDS, triethylamine, and diisopropyl amine etc. The organic solvent used in this reaction can be selected from methanol, ethanol, n-butanol, diethyl ether, diisopropyl ether, ethyl acetate, and tetrahydrofuran solvent. The reducing agent can be used as lithium aluminium hydride, sodium borohydride, DIBAL, etc. or any reducing agent known in the art. In step-1, the reaction can be carried out about 0 to 65° C. The compound of formula (A) may be in isolated or non-isolated form. The compound of formula (A) can be recrystallized with the use of solvent or mixture of solvents known in the art.

The racemic amine can be converted to their chiral acid salts i.e. the compound of formula (B). The compound I salts include, but not limited to salts formed with alanine, aspartic acid, glutamine, N-acetyl-leucine, phenylethylamine, mandelic acid, tartaric acid and citric acid. The preferred acid for preparation of amine salt is N-acetyl-L-leucine. This reaction can be carried out in any water miscible or immiscible solvent/s known in the art.

Another aspect of this invention is to provide an improved process for preparation of apremilast i.e. compound of formula (C) from amine salt. The chiral amine salt is reacted with 3-acetamidophthalic anhydride in presence of a solvent or mixture of solvents or an acid or base condition. The solvents include, but not limited to water miscible or immiscible solvents. Organic acid or inorganic acid, such as acetic acid, trifluoroacetic acid, hydrochloric acid, sulfuric acid etc.

After completion of reaction, the resultant solid can be treated with an organic solvent or mixture of solvents. The solvent include, but not limited to ketone, alcohol, hydrocarbon, ether, water, ester, nitrile, halohydrocarbon and amide solvents or water miscible or immiscible solvents known in the art.

The precipitated final compound can be treated with solvents include, not limited to, ketone, alcohol, hydrocarbon, ether, water, ester, nitrile, halohydrocarbon and amide solvents or water miscible or immiscible solvents known in the art.

In another aspect, the apremilast obtained by the process of invention can be converted into novel polymorphs.

This present invention also provides novel polymorphs of apremilast.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Solvent medium and mode of crystallization play very important role in obtaining a new salt or a crystalline form over the other.

The present invention provides a novel polymorphs of apremilast, which are stable throughout its shelf life and is clinically bioequivalent under FDA standards for this product.

The present invention also provides a crystal of Form M of apremilast. The crystal of Form M of apremilast is stable.

The present invention provides processes for preparation of novel polymorphs of apremilast, wherein, the apremilast can be treated with a water miscible or water immiscible solvents selected from ketone, ester, hydrocarbons, amide, halocarbons, alcohol and ether solvents at a particular temperature. The resulting solid is filtered, washed and dried at higher temperature. The solvent/s have treated can be selected from water, acetone, diethylketone, methylisobutylketone, N-methylpyrrolidone, ethylacetate, n-hexane, n-heptane, toluene, xylene, cyclohexane, N,N'-Dimethylformamide, N,N'-Dimethylacetamide, chloroform, dichloromethane, methanol, ethanol, n-propanol, isopropanol, n-butanol, isobutanol, diethyl ether, isopropyl ether, dioxane, tetrahydrofuran and acetonitrile in a single solvent or mixture of solvents said herein. The temperature used in the process of present invention may be −5 to 100° C.

The resultant solid analyzed by different techniques such as, thermogravimetric analysis, differential scanning calorimetry, moisture content, powder x-ray diffraction and other available analytical techniques well-known in the literature with the available procedures.

The present invention provides new and stable polymorphs of apremilast. These polymorphs are stable and viable at any scale. More specifically, a novel polymorph apremilast, designated as Form M, is stable at longer durations as per ICH and USP guidelines.

The Form M of apremilast has good solubility in various medium such as water, hydrochloric acid, acetate Buffer, and phosphate Buffer at different pH.

The term "stable" with respect polymorph or to a drug dosage form, refers to the chemical and physical integrity of the polymorph or dosage unit and, when appropriate, the ability of the dosage unit to maintain protection against microbiological contamination.

Figure 15:
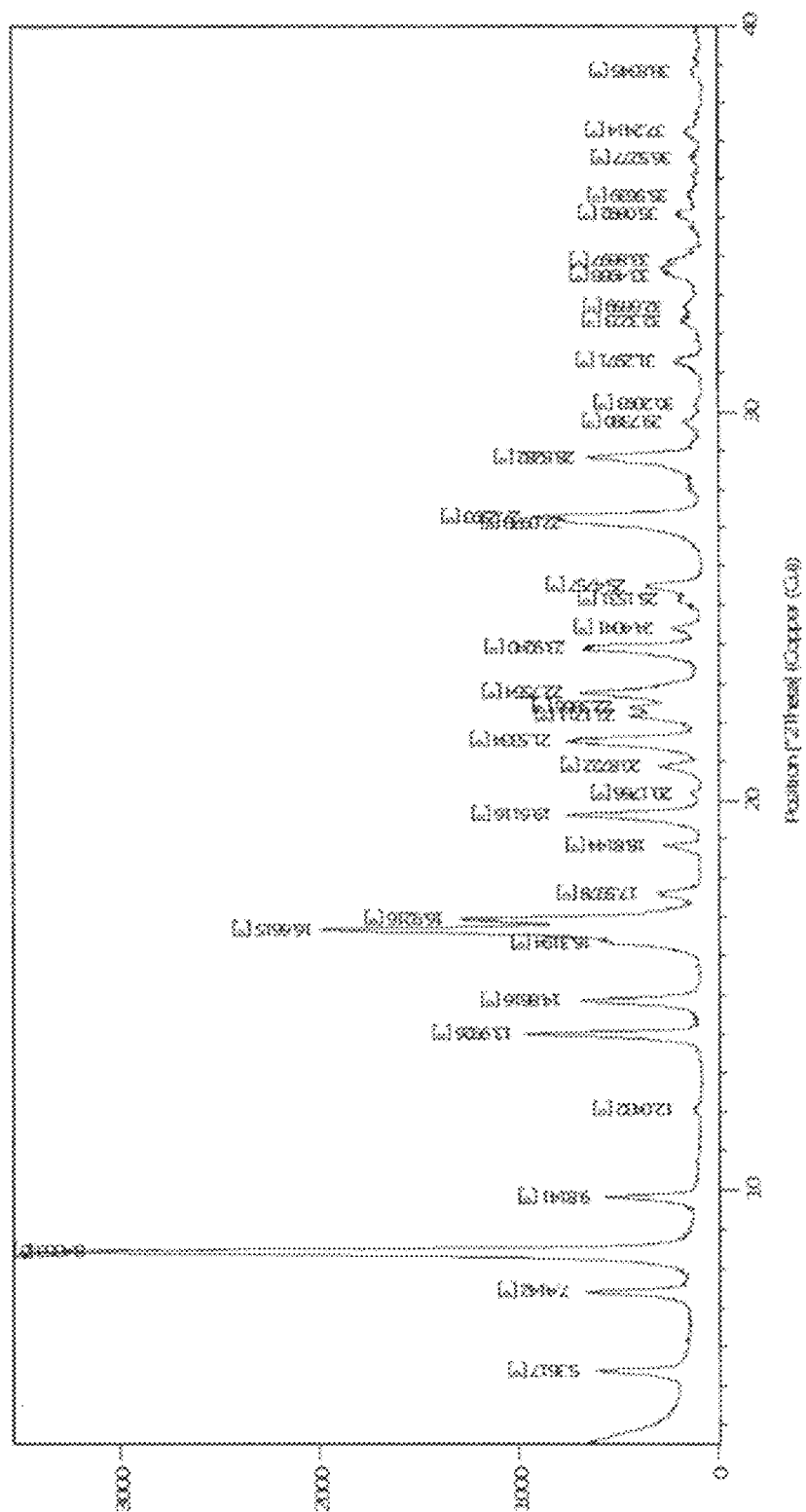
FIG. 15 depicts Powder X-Ray diffraction pattern of Form M of apremilast (25° C./60% RH/2M)
Figure 16:
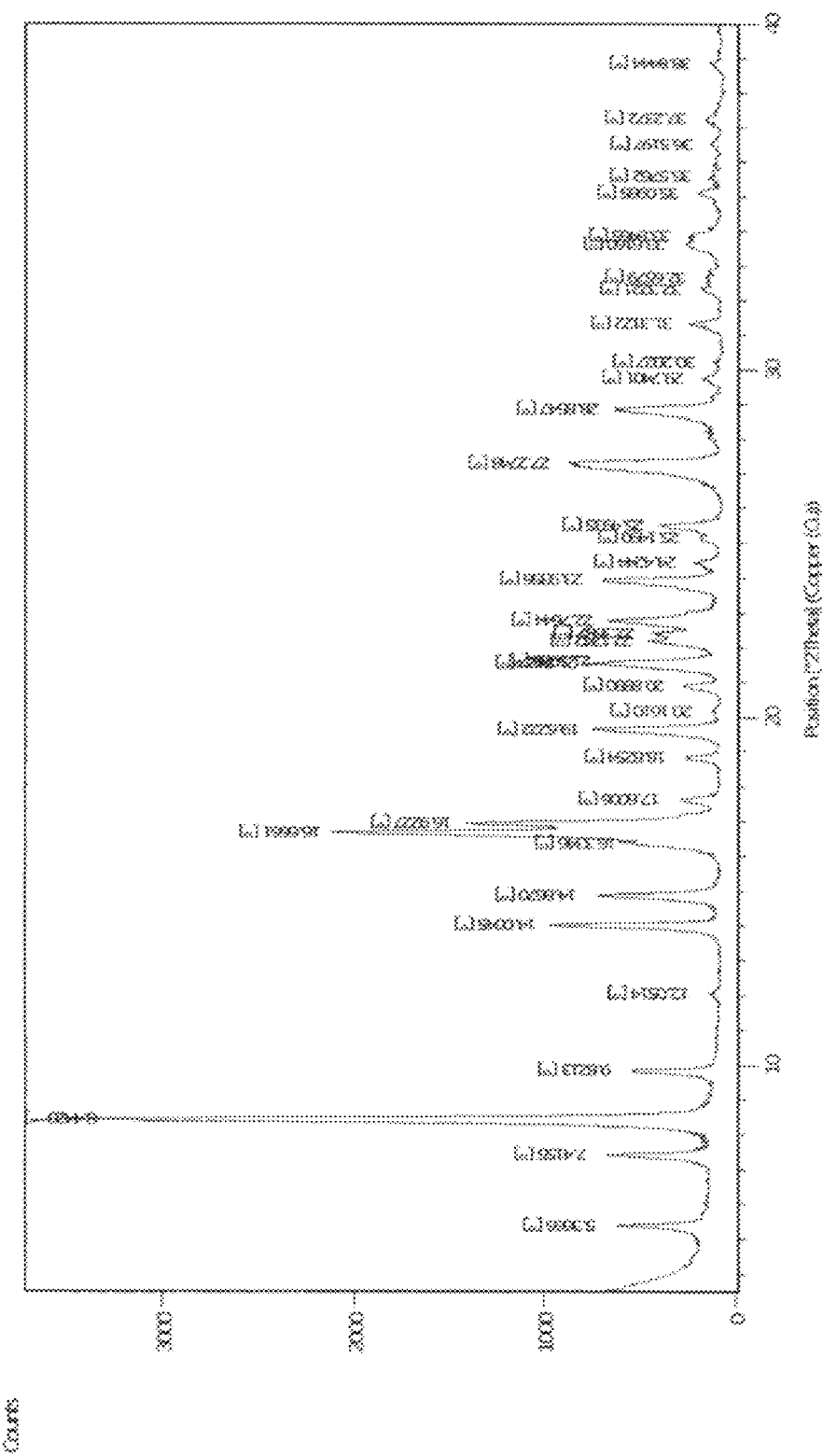
FIG. 16 depicts Powder X-Ray diffraction pattern of Form M of apremilast (40° C./75% RH/2M)

The Form M of apremilast is stable at different set of conditions such as 25° C. to 40° C. temperature, 5% to 75% humidity (RH) for durations as depicted in FIG. 15 and FIG. 16.

The process of the novel polymorphs of apremilast is feasible at all scale and avoids use of harmful chemicals and solvents. This process for preparation of Form M of apremilast is eco-friendly cost effective, green and industrial applicable.

Molar equivalents of solvent/s employed for this invention vary with respect to apremilast equivalents.

In the present invention the content of water in apremilast ranges from about 0.1% to about 6.0%. The isolation of this crystalline solid polymorph is carried out by the conventional techniques known in the prior art such as filtration, concentration, and evaporation etc.

In the present invention, apremilast used as a starting material is obtained by the processes known in the art. Thus, apremilast prepared by U.S. Pat. No. 6,962,940 or 7,427,638 can be used as starting materials for the preparation of the novel polymorphs of apremilast of the present invention.

Figure 8:
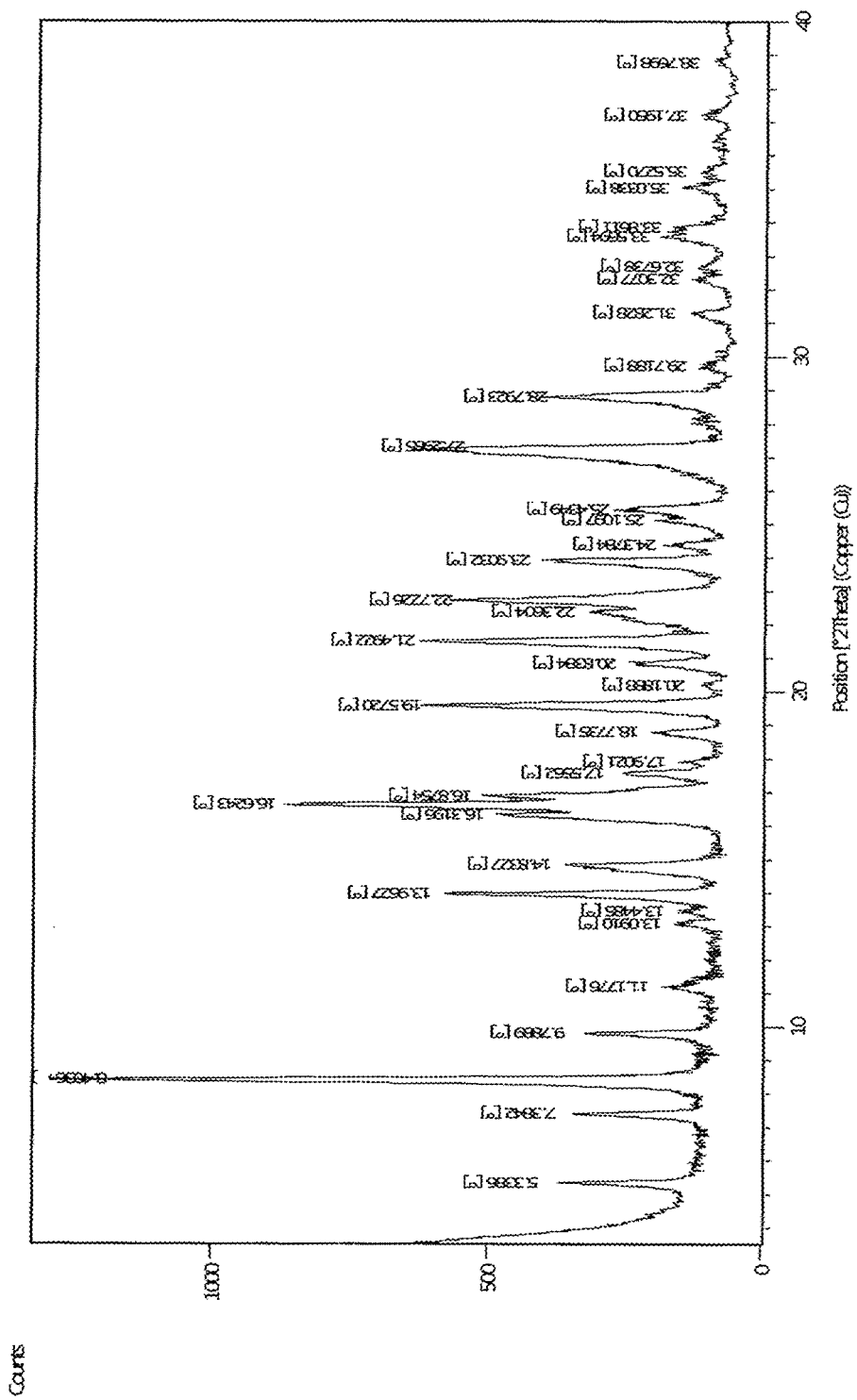
FIG. 8 depicts Powder X-Ray diffraction of Form M of apremilast.
Figure 12:
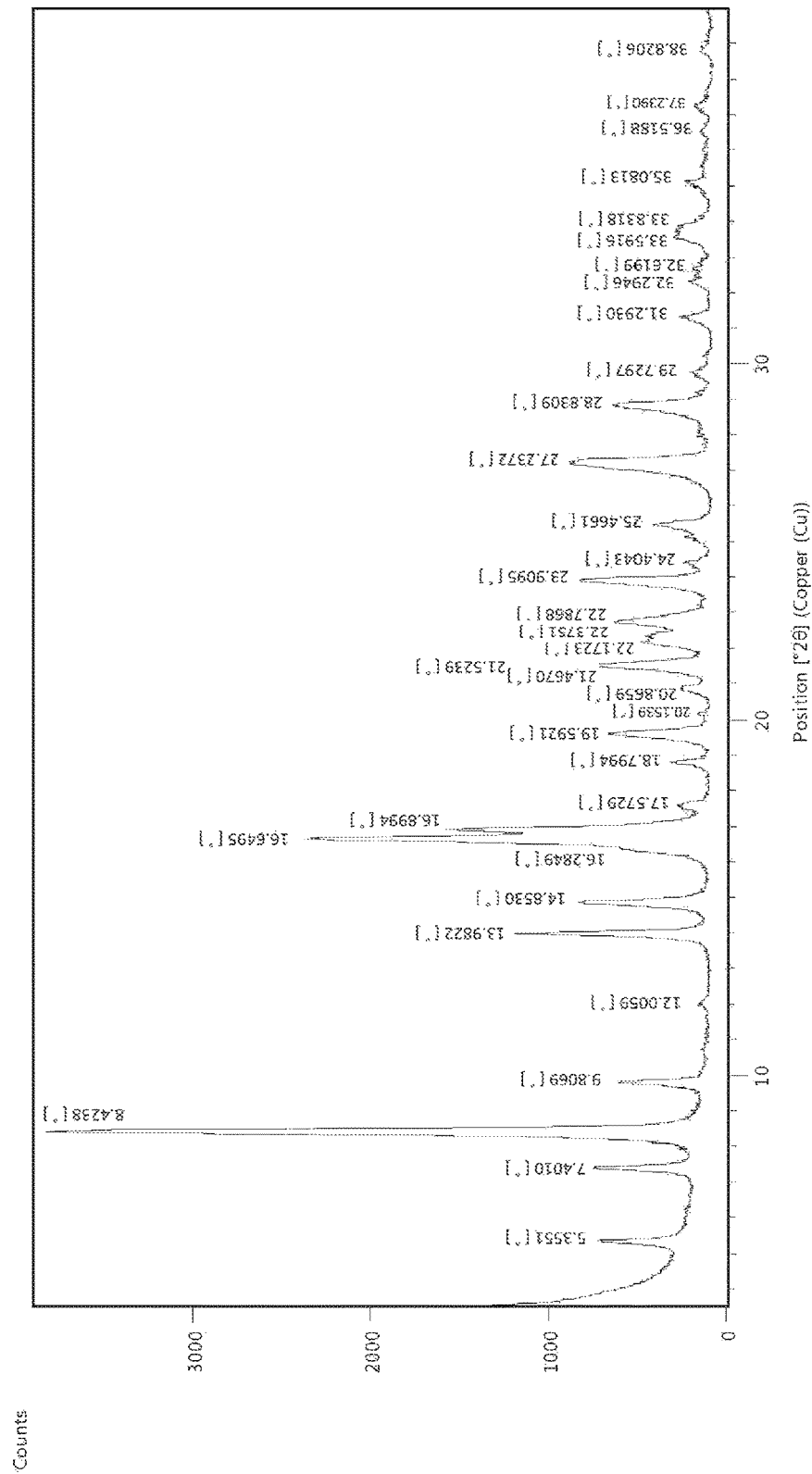
FIG. 12 depicts Powder X-Ray diffraction pattern of Form M of apremilast prepared by acetone and water.
Figure 13:
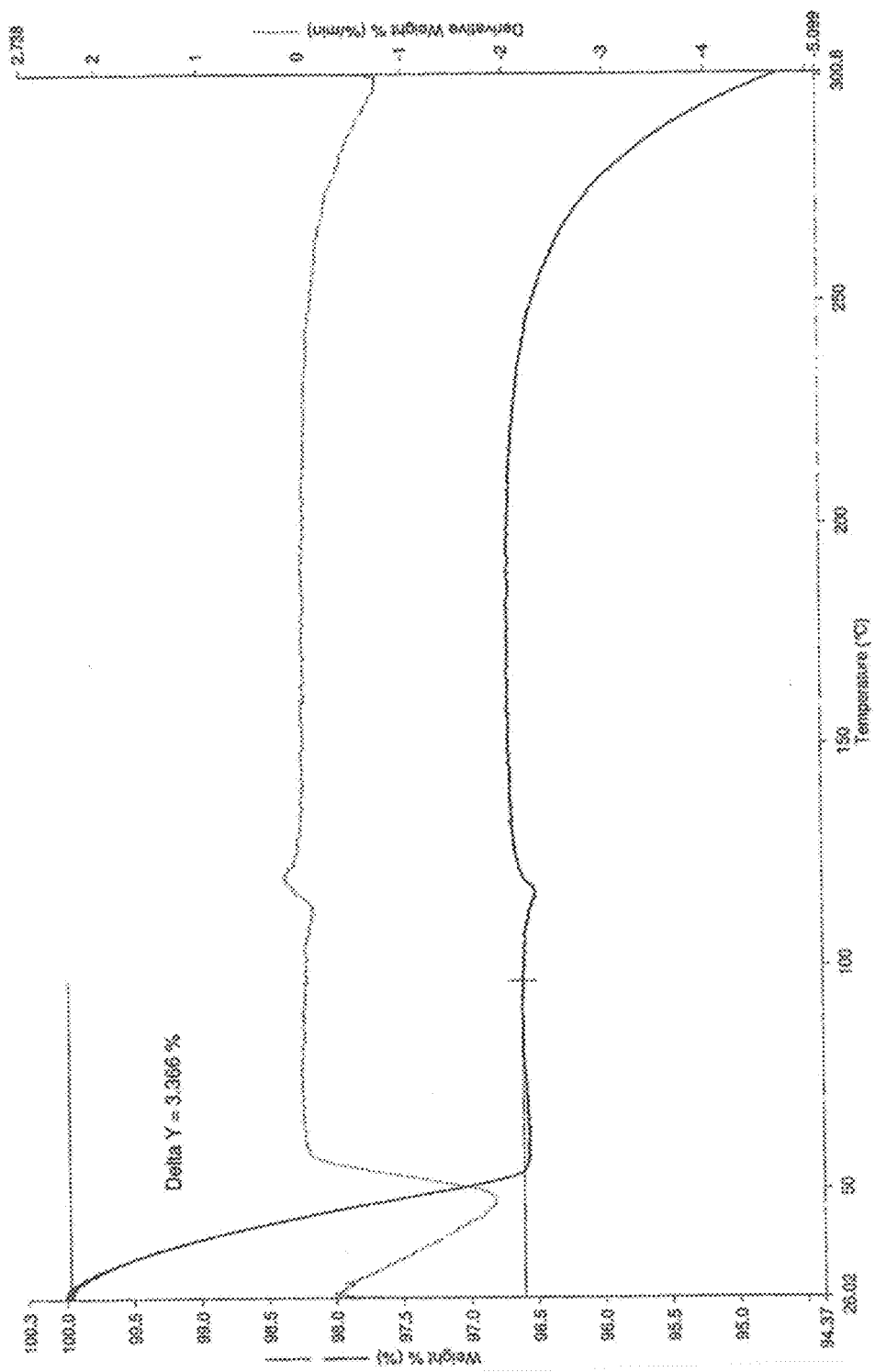
FIG. 13 depicts TG thermogram of Form M of apremilast prepared by acetone and water.
Figure 14:
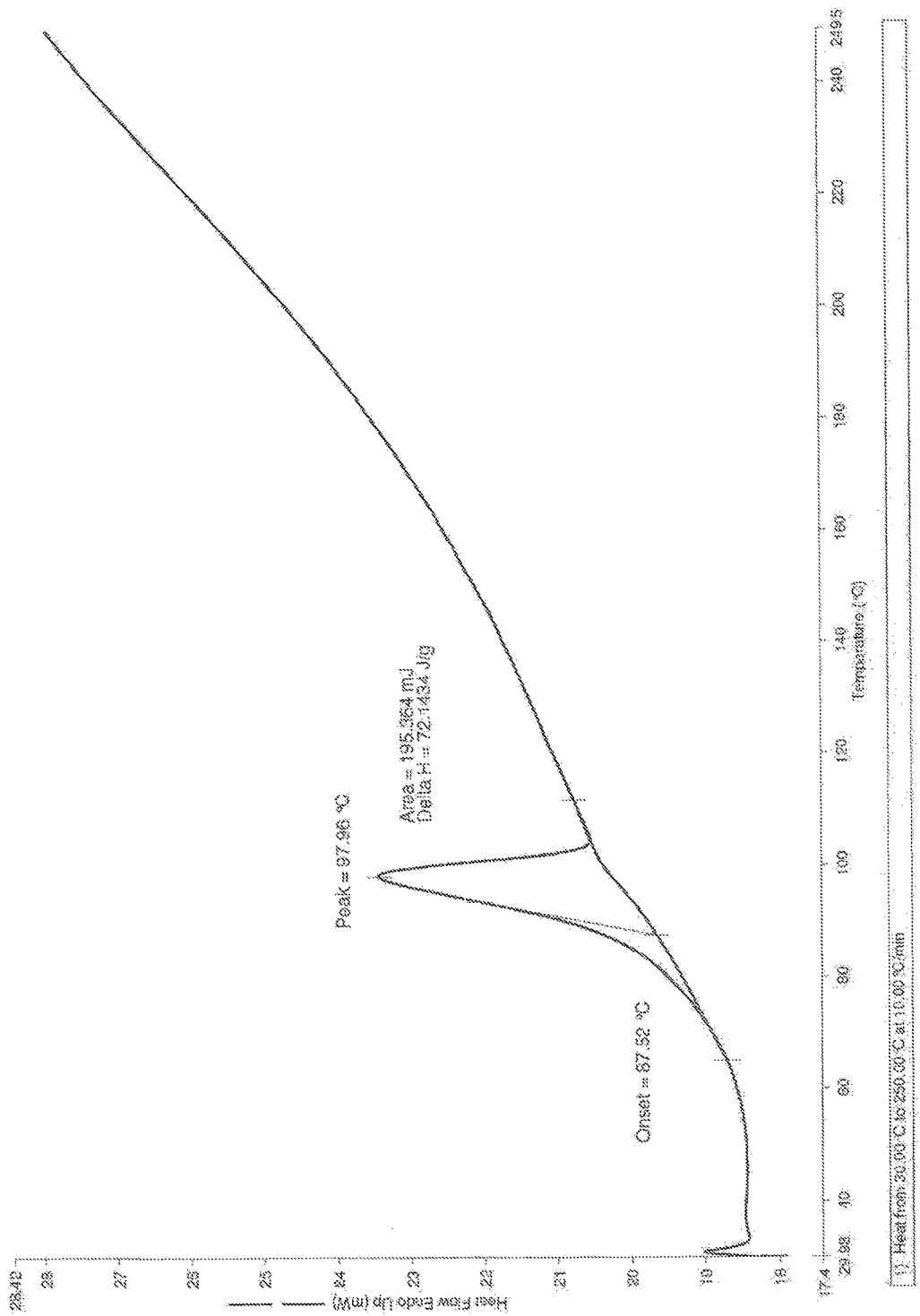
FIG. 14 depicts DSC thermogram of Form M of apremilast prepared by acetone and water.

According to another aspect of the present invention, a stable crystalline Form M of apremilast characterized by at least one of the following properties is provided:
i) Powder X-Ray diffraction pattern as described in FIG. 8 and or FIG. 12 having peaks at 5.3, 8.4, 9.8, 13.98, 14.85, 16.64, 19.59, 21.46, 27.23±0.2° 2theta values;
ii) Thermogravimetric analysis curve (TGA) shows in FIG. 13;
iii) Differential scanning calorimetric (DSC) thermogram as depicted in FIG. 14.

Analytical Methods
1) Powder X-Ray Diffraction (PXRD)

Using a PANalytical X'Pert powder diffraction meter, the x-ray powder diffraction pattern was measured at room temperature using a Cu K$\alpha$ filled tube (45 kV 40 mA) as the x-ray source. Data collection was done in 2theta continuous scan mode in the range of 3.5° to 40°.

For crystal study, PXRD data of Form M of apremilast were collected at 293(2) K on a Bruker D8 Advance diffractometer operating in the Bragg-Brentano geometry with CuK$\alpha$ radiation ($\lambda$=1.5418 Å). The PXRD patterns were indexed using the NTREOR code in the program EXPO 2014 yielding monoclinic unit cells. Given the volume of unit cell and consideration of density, the number of formula units in the unit cell turned out as Z=2. The unit cell parameters (FIGS. 17, 17A & 17B) and space group (P2$_1$) assignments were validated by a Le-Bail fit of PXRD data using a pseudo-Voigt peak profile function with FOX. Structure solution was carried out by global optimization of structural models in direct space based on a Monte Carlo search using the simulated annealing technique (in parallel tempering mode), as implemented in the program FOX. The best solution (i.e., the structure with lowest Rwp) was used as the structural model of Form M for Rietveld refinement, which was carried out using the GSAS program. The final Rietveld plots of Form M showed good agreement between the observed P-XRD profile and powder pattern calculated.

2) Thermogravimetric Analysis

Thermogravimetric analysis was performed using a Pyris 1 TGA PERKIN ELMER measurement unit. 2-5 mg samples were placed in open Platinum pans and heated from 25° C. to 300° C. in a dry nitrogen atmosphere at a heating rate of 10° C./min.

3) Differential Scanning Calorimetry

Differential Scanning calorimetry was performed using a Diamond DSC PERKIN ELMER differential instrument. 2-3 mg samples were placed in crimped aluminum pans and heated from 30° C. to 250° C. in a dry nitrogen atmosphere at a heating rate of 10° C./minute.

4) Water Content

Karl-Fischer auto titrator Metrohm Titrando was used for detection of water content as per methods known in the art.

5) Nuclear Magnetic Resonance $H^1$NMR and $^{13}$CMR was performed using Bruker NMR instrument at 400 MHz in CDCl3 as solvent.

6) Infra-Red Spectroscopy

IR spectroscopy was performed using a Spectrum 400 using a neat liquid sample or dispersion of solid sample material in KBr.

7) Mass Spectrometry

Measurements of mass of sample which is subject to a temperature program were obtained on Waters.

The described novel polymorphs of apremilast may be used as a pharmaceutical composition with the particular dosage forms for treating the psoriasis or psoriasis related disorders.

Pharmaceutical formulations novel polymorphs of apremilast according to the present invention comprises of one or more pharmaceutically acceptable carriers or excipients such as binders, fillers, disintegrants, surfactants, lubricants or combinations thereof and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared.

Binders for use in the formulations of the present invention include binders commonly used in the formulation of pharmaceuticals. Examples of binders for use in accordance with the present invention include but are not limited to cellulose derivatives (including hydroxypropyl cellulose, hydroxypropyl methylcellulose, methylcellulose, and sodium carboxymethyl cellulose), glycol, sucrose, dextrose, corn syrup, polysaccharides (including acacia, targacanth, guar, alginates and starch), corn starch, pregelatinized starch, modified corn starch, gelatin, polyvinylpyrrolidone, polyethylene, polyethylene glycol, combinations thereof and the like.

Fillers or diluents for use in the formulations of the present invention include fillers or diluents typically used in the formulation of pharmaceuticals. Examples of fillers or diluents for use in accordance with the present invention include but are not limited to sugars such as lactose, dextrose, glucose, sucrose, cellulose, starches and carbohydrate derivatives, polysaccharides (including dextrates and maltodextrin), polyols (including mannitol, xylitol, and sorbitol), cycludextrins, calcium carbonates, magnesium carbonates, microcrystalline cellulose, combinations thereof, and the like. In certain preferred embodiments the filler or diluent is lactose, microcrystalline cellulose, or combination thereof. Several types of microcrystalline cellulose are suitable for use in the formulations described herein, for example, microcrystalline cellulose selected from the group consisting of Avicel™ types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate.

Disintegrants for use in the formulations of the present invention include disintegrants commonly used in the formulation of pharmaceuticals. Examples of disintegrants for use in accordance with the present invention include but are not limited to starches, clays, alginates and gums and crosslinked starches, celluloses and polymers, microcrystalline cellulose, croscarmellose sodium, alginic acid, sodium alginate, crosprovidone, agar and related gums, sodium starch glycolate, corn starch, potato starch, sodium starch glycolate, Veegum HV, methylcellulose, agar, bentonite, carboxymethylcellulose, alginic acid, guar gum combinations thereof, and the like.

Surfactants for use in the formulations of the present invention include surfactants commonly used in the formulation of pharmaceuticals. Examples of surfactants for use in accordance with the present invention include but are not limited to ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, combinations thereof, and the like.

Lubricants for use in the formulations of the present invention include lubricants commonly used in the formulation of pharmaceuticals. Examples of lubricants for use in accordance with the present invention include but are not limited to magnesium carbonate, magnesium laurylsulphate, calcium silicate, talc, fumed silicon dioxide, magnesium stearate, calcium stearate, stearic acid, sodium stearyl fumarate, polyethylene glycol, sodium lauryl sulphate, magnesium lauryl sulphate, sodium benzoate, colloidal silicon dioxide, magnesium oxide, microcrystalline cellulose, starches, mineral oil, waxes, glyceryl behenate, polyethylene glycol, sodium acetate, sodium chloride, combinations thereof, and the like.

Other polymers commonly used as excipients include but are not limited to methylcellulose (MC), ethylcellulose (EC), hydroxyethylcellulose (HEC), methyl hydroxyethylcellulose (MHEC), hydroxypropyl cellulose (HPC), hydroxypropyl methylcellulose (HPMC), sodium carboxymethylcellulose (NaCMC), and the like. These polymers, either alone or in various combinations, may serve multiple purposes including but not limited to controlling release of the formulations of the present invention.

The present invention will now be further illustrated by reference to the following examples, which do not limit the scope of the invention any way.

Example 1—Step-I: Process for Preparation of 2-(-3-ethoxy-4-methoxyphenyl)-1-(methanesulfonyl)-eth-2-ylamine In a 2 liter round bottom flask, 300 ml of tetrahydrofuran was charged followed by 32 gms of dimethylsulfone. This reaction mass was cooled for 15 to 20 minutes at 0° C. After cooling, potassium-hexamethyldisilazane was added followed by 20 ml of tetrahydrofuran. The reaction mass was stirred for an hour at 0 to 5° C. After stirring, 30 gms of 3-ethoxy-4-methoxybenzonitrile was dissolved in 90 ml tetrahydrofuran and was added to the above reaction mass. The reaction mass was stirred for 30 minutes. After stirring, 23 gms of sodium borohydride was added followed by tetrahydrofuran and acetic acid and the total reaction mass was stirred for 2 hours at 0 to 5° C. After completion of reaction, sodium hydroxide solution was added to it and stirred for 30 minutes. The reaction mass was warmed and further heated for 3 to 4 hours at 60 to 62° C. After completion of reaction, the reaction solution was allowed to cool to room temperature for half an hour. The layers were separated. The aqueous layer was treated with ethyl acetate and the organic layer was treated with hydrochloric acid. The solution was stirred. The layers were separated. The organic layer was treated with 20% sodium hydroxide solution and the solid was precipitated. The solid was filtered, washed and dried at 50° C. and further 30.2 gms of material was unloaded.

Step-II: Process for Preparation of 2-(-3-ethoxy-4-methoxyphenyl)-1-(methanesulfonyl)-eth-2-ylamine N-acetyl-L-leucine salt In a 500 ml round bottom flask, 200 ml of methanol was added followed by 20 gms of 2-(3-ethoxy-4-methoxyphenyl)-1-(methanesulfonyl)-eth-2-ylamine. The reaction mass was stirred and 76 gms of N-Acetyl-L-Leucine added and reaction mass was stirred. The reaction mass was heated for 2 hours at 60 to 65° C., After heating, the reaction mass was cooled at room temperature and it was stirred at room temperature for 3 to 4 hours. The slurry was filtered. Washed with 30 ml methanol, material was unloaded and dried under vacuum for 2 hours at 45° C. Yield: 14.36 gm. Further, this material is purified with methanol.

Step-III: Process for Preparation of Apremilast

In a 250 ml round bottom flask, 50 ml acetic acid was charged followed by 10 gms of 2-(-3-ethoxy-4-methoxyphenyl)-1-(methanesulfonyl)-eth-2-ylamine N-acetyl-L-leucine salt and it was stirred at room temperature for a few minutes. Then 4.82 gms of 3-acetamidophthalic anhydride was added and reaction mass was heated for 11 to 12 hours at 80 to 90° C. The solvent was removed under vacuum and ethyl acetate was added followed by sodium bicarbonate solution. The layers were separated. The organic layer was washed and solvent was evaporated under vacuum. In the distilled residue, 90 ml ethanol and 30 ml acetone added and was stirred it for 2 hours at room temperature. The solid was precipitated. The solid was filtered and washed with ethanol. The material was unloaded and dried under vacuum for longer hours at 60° C. Yield: 6.41 gm. This material will be crystallized using a solvent or mixture of solvents known in the art.

Example 2—Step-I: Process for Preparation of 2-(-3-ethoxy-4-methoxyphenyl)-1-(methanesulfonyl)-eth-2-ylamine In a flask, 5 liters of tetrahydrofuran was charged followed by 1.06 kg of dimethylsulfone. This reaction mass was cooled for 25 to 30 minutes at 0° C. After cooling, 1M potassium-hexamethyldisilazane was added followed by 10 liters of tetrahydrofuran. The reaction mass was stirred for an hour at 0 to 10° C. After stirring, 1 kg of 3-ethoxy-4-methoxybenzonitrile was dissolved in 2 liters tetrahydrofuran and was added to the above reaction mass. The reaction mass was stirred for 30 minutes and cooled. After cooling, 0.433 kg of sodium borohydride was added followed by tetrahydrofuran and 5 liters of acetic acid and the total reaction mass was stirred for 3-4 hours at 0 to 10° C. After completion of reaction, sodium hydroxide solution was added to it and stirred for 45 minutes. The reaction mass was warmed and further heated for 3 to 4 hours at 60 to 65° C. After completion of reaction, the reaction solution was allowed to cool to room temperature for half an hour. The layers were separated. The combined organic layer was treated with aq. HCl and water was added to the concentrated mass. The aqueous layer was treated with ethyl acetate. Finally sodium hydroxide solution was added to the aqueous layer and solid was precipitated. The solid was filtered, washed with water and dried at 50° C. and further 1.0 kg (65%) of material was unloaded.

Step-II: Process for Preparation of 2-(-3-ethoxy-4-methoxyphenyl)-1-(methanesulfonyl)-eth-2-ylamine N-acetyl-L-leucine salt In a flask, 10 liters of methanol was added followed by 1 kg of 2-(3-ethoxy-4-methoxyphenyl)-1-(methanesulfonyl)-eth-2-ylamine. The reaction mass was stirred and 0.38 kg of N-Acetyl-L-Leucine added and reaction mass was stirred. The reaction mass was heated for 2-3 hours at 60 to 70° C. After heating, the reaction mass was cooled at room temperature and it was stirred at room temperature for 3 to 4 hours. The slurry was filtered and washed with 1.5 liters of methanol. The wet cake was washed with adequate quantities of methanol and water. Material was unloaded and dried under vacuum for 2 hours at 45° C. Yield: 0.60 kg (73.5%).

Step-III: Process for Preparation of Apremilast

In a flask, 5 liters of acetic acid was charged followed by 1 kg of 2-(3-ethoxy-4-methoxyphenyl)-1-(methanesulfonyl)-eth-2-ylamine N-acetyl-L-leucine salt and it was stirred at room temperature for a few minutes. Then 0.482 kg of 3-acetamidophthalic anhydride was added and reaction mass was heated for 11 to 12 hours at 75 to 90° C. Cool the reaction mass. The solvent was removed under vacuum and ethyl acetate was added followed by sodium bicarbonate solution. The layers were separated. The slurry of carbon in ethyl acetate is added to the above reaction mass. Stir and filter the mass. The organic layer was washed with ethyl acetate and solvent was evaporated under vacuum. In the residue, is added 5 liters of acetone and heated to 40-50° C. The clear solution is filtered through micron paper. The solution is partially distilled and 6 liters of methanol is added to it. The solution is seeded with Apremilast. The solid was precipitated. The slurry is stirred for 3-4 hours at room temperature and was filtered and washed with methanol. The material was unloaded and dried under vacuum for longer hours at 50-60° C. Yield: 0.75 gm (72.8%).

The $H^1$NMR data is (CDCl3) δ: 1.471, t, 3H; 2.264, s, 3H; 2.884, s, 3H; 3.851, s, 3H; 3.73-3.77, dd, 1H; 4.08-4.13, q, 2H; 4.52-4.58, dd, 1H; 5.85-5.89, dd, 1H; 6.83-8.75, m, 6H; 9.461, s, 1H. The $C^{13}$MR data is (CDCl3) δ: 14.58, 24.84, 41.51, 48.38, 54.27, 55.81, 64.38, 111.30, 112.26, 114.99, 118.08, 120.17, 124.80, 135.99, 137.47, 148.48, 149.58, 167.36, 169.07, and 169.36. DSC at 159.14° C.

Example 3—Process for Preparation of Form L of Apremilast

Figure 5:
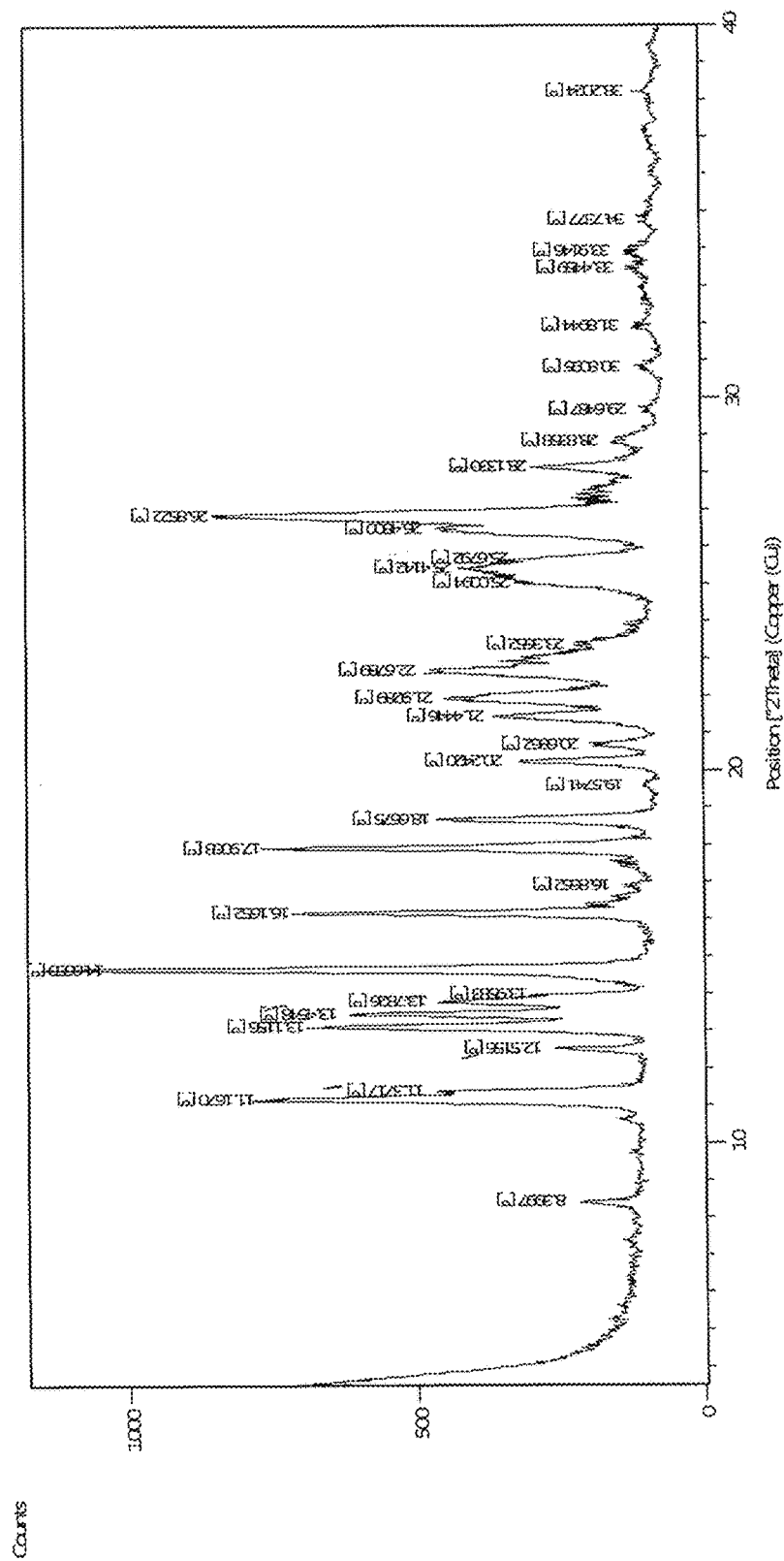
FIG. 5 depicts Powder X-Ray diffraction pattern of Form L of apremilast.
Figure 6:
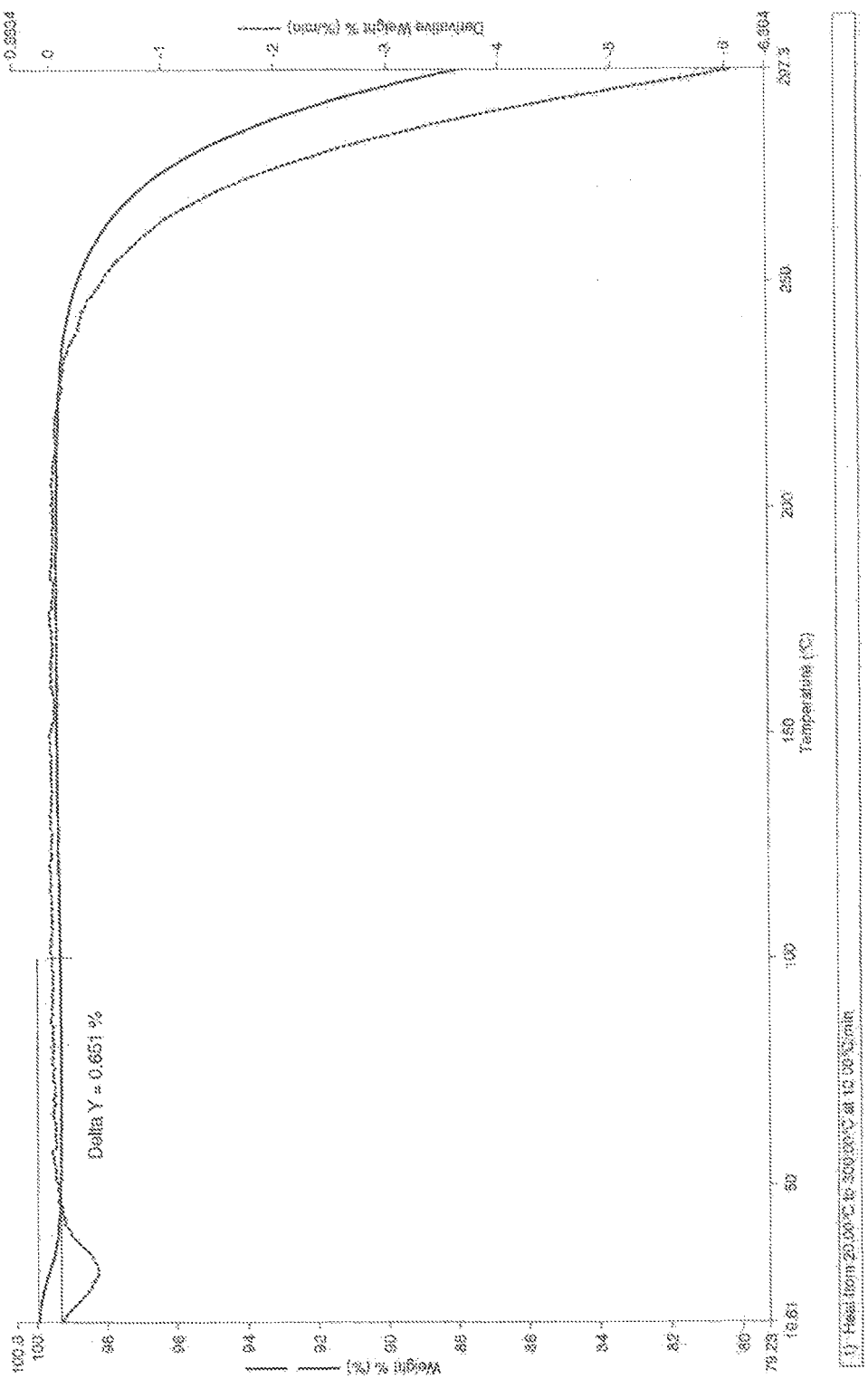
FIG. 6 depicts TG thermogram of Form L of apremilast.
Figure 7:
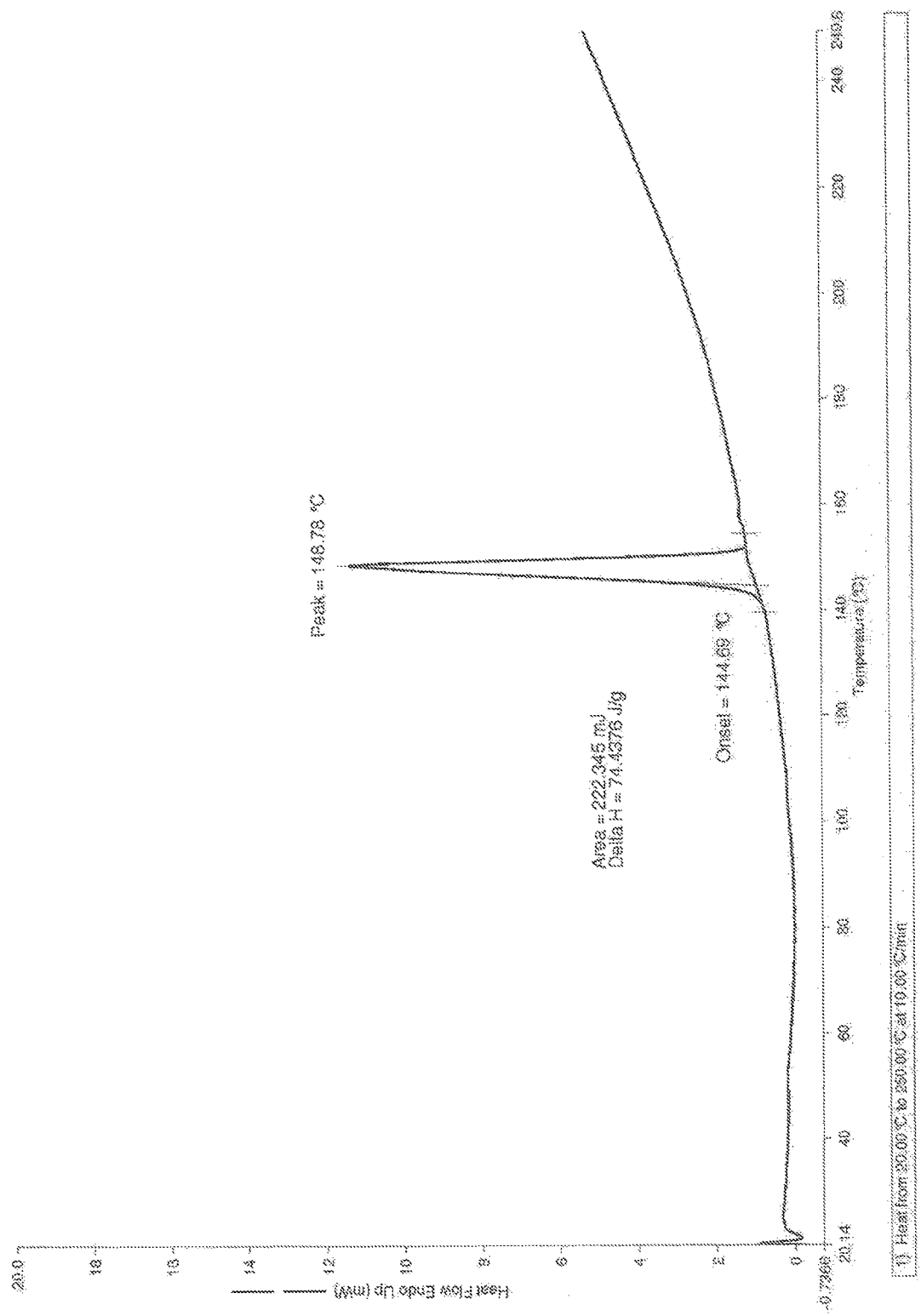
FIG. 7 depicts DSC thermogram of Form L of apremilast.

In a 2 L round bottom flask, 10.3 gm of apremilast was added followed by 14 ml of N,N-dimethylformamide. The reaction temperature was raised to 90° C. and was stirred for 30 minutes. After stirring, the reaction mass was stirred for 30 minutes at 30 to 40° C. The 500 ml distilled water was slowly added and stirred for 9 to 10 hours at room temperature. After stirring, the resultant solid was filtered and washed with 100 ml water. The solid was dried for 8 hours at 45° C. Yield: 9.6 gm, Moisture content: 0.651%. The Powder X-Ray diffraction pattern, TG thermogram and DSC thermogram had obtained identical with FIGS. 5, 6 and 7 respectively.

Example 4—Process for Preparation of Form M of Apremilast

Figure 9:
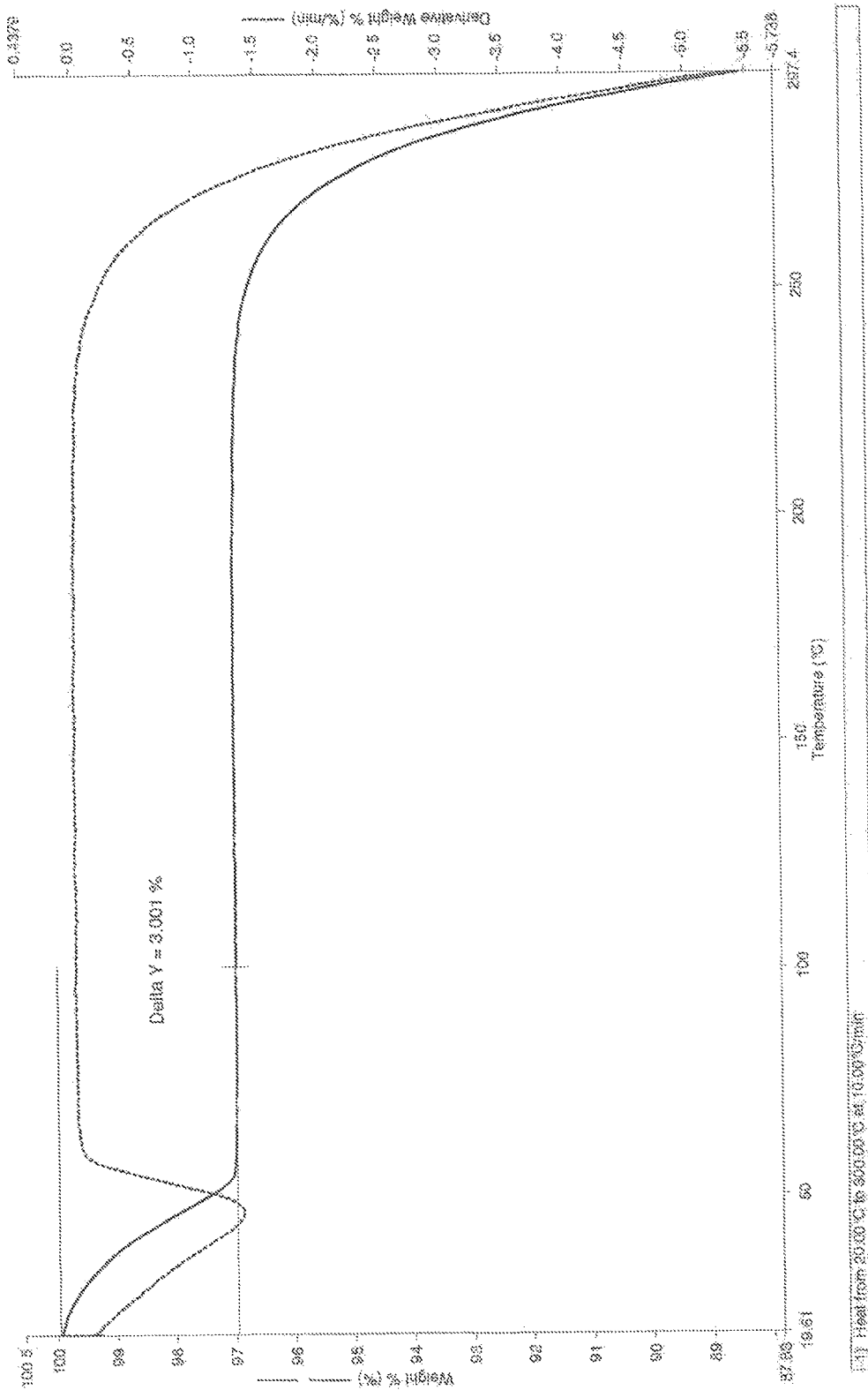
FIG. 9 depicts TG thermogram of Form M of apremilast.

In a 2 L round bottom flask, 10 gm of apremilast was added followed by 10 ml of N, N-dimethylformamide. The reaction temperature was raised to 80° C. and was stirred for 10 minutes. After stirring, the reaction mass was cooled down to 25 to 30° C. and 500 ml water was added in dropwise fashion. The slurry was stirred overnight at 25° C. The solid was filtered under vacuum and was dried under vacuum for 15 to 20 hours at 45° C. Yield: 8.5 gm. Moisture content: 3 to 3.28%. The P-X Ray diffraction TGA data had obtained identical with FIGS. 8 and 9 respectively.

Example 5—Process for Preparation of Form N of Apremilast

Figure 10:
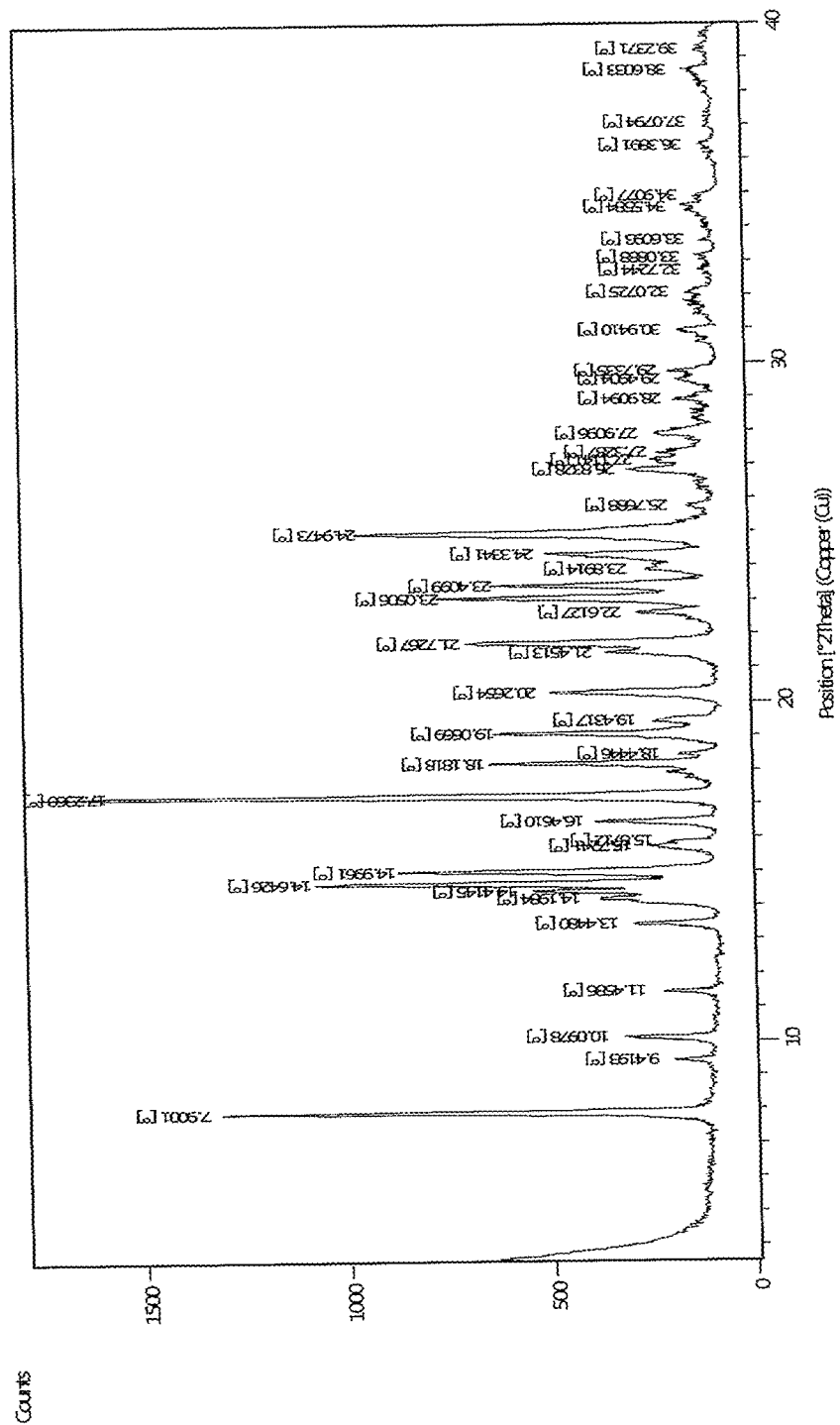
FIG. 10 depicts Powder X-Ray diffraction pattern of Form N of apremilast.

In a 500 ml round bottom flask, 4 gm of apremilast was added followed by 10 ml of chloroform and 155 ml of cyclohexane. The reaction mass stirred for 26 to 27 hours at 25 to 30° C. and solid was generated. The 0.2 gm of apremilast was seeded and solid material was filtered. The solid was dried under vacuum for 10 minutes at room temperature and then in vacuum for 14 to 15 hours at 45° C. Yield: 3.1 gm. DSC data: 155.98 to 157.72° C. The Powder X-Ray diffraction pattern had obtained identical with FIG. 10 respectively.

Example 6—Process for Preparation of Form O of Apremilast

Figure 11:
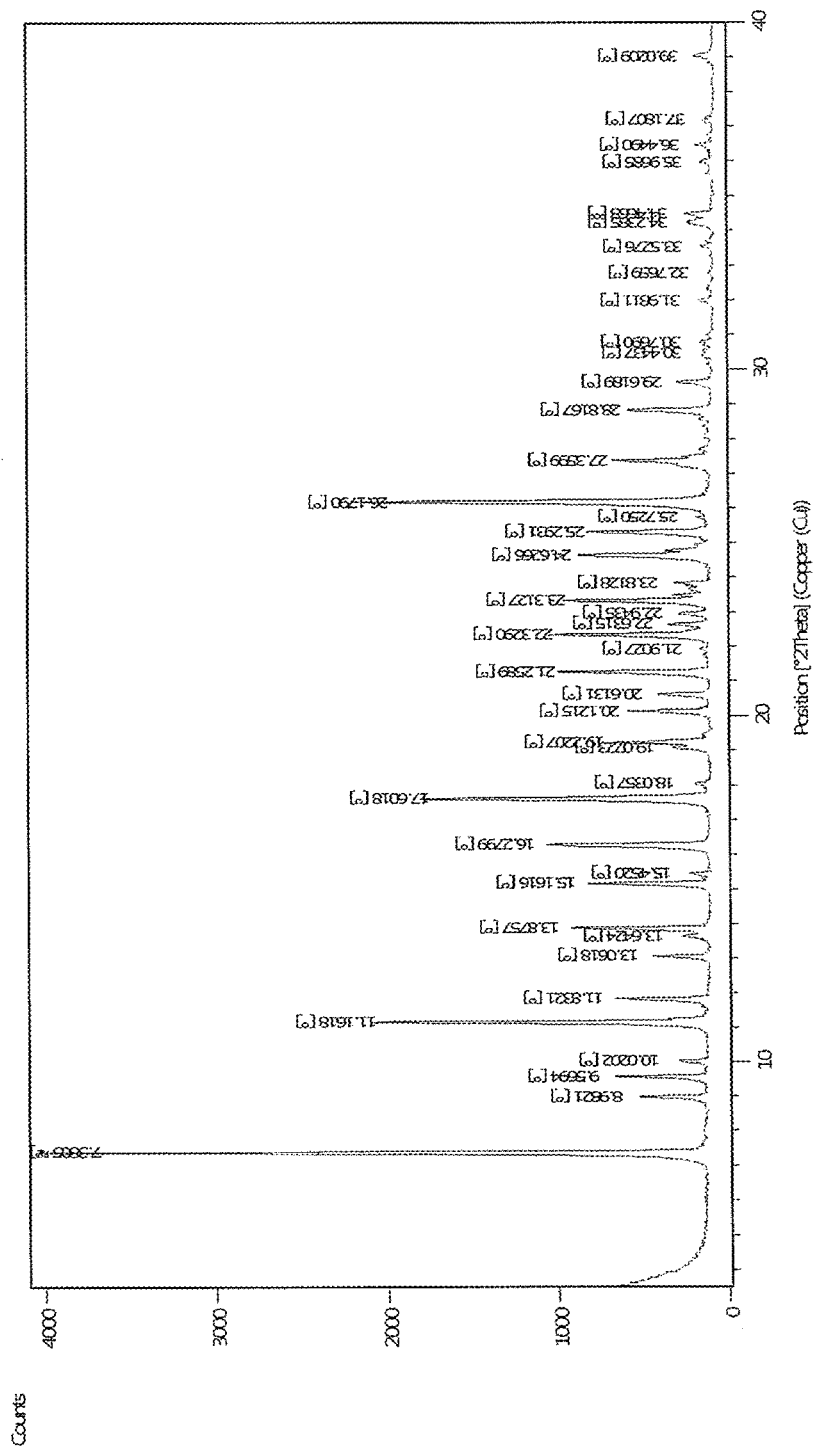
FIG. 11 depicts Powder X-Ray diffraction pattern of Form O of apremilast.

In a 100 ml round bottom flask, 3 gm of apremilast was added followed by 5 ml of N-methylpyrrolidone and was heated to 60° C. for 5 minutes. The solid material was filtered at room temperature. The filtrate was left for slow evaporation in a freeze for near about 24 hours at −5 to −10° C. The precipitate was filtered and dried in a vacuum oven for 4 hours at 45° C. The dried product was further dried for 7 hours at 45° C. Yield: 1.49 gm. The Powder X-Ray diffraction pattern had obtained identical with FIG. 11 respectively.

Example 7—Process for Preparation of Form M of Apremilast

In a 500 ml round bottom flask, 100 ml acetone was charged followed by addition of 25 gm of apremilast and was heated at 45° C. to 55° C. to form clear solution. This clear solution was filtered through filter paper and washed with acetone. In another flask, DM water was taken and was chilled to lower temperature. The above acetone solution was added to the chilled water slowly. After addition, reaction mass was maintained for 14 to 21 hours at lower temperature. The solid was precipitated and was filtered, washed with DM water and dried under vacuum at below 45° C. Yield of the solid was 21.5 gm. The Powder X-Ray diffraction pattern, TG, and DSC thermogram had obtained identical with FIGS. 12, 13 and 14 respectively.

Example 8—Process for Preparation of Form M of Apremilast

In a 500 ml round bottom flask, 100 ml aqueous acetone solution was charged followed by addition of 25 gm of apremilast and was heated at 45° C. to 55° C. to form clear solution. This clear solution was filtered through filter paper and washed with acetone. In another flask, DM water was taken and was chilled to lower temperature. The above acetone solution was added to chilled water slowly. After addition, reaction mass was maintained for 14 to 18 hours at lower temperature. The solid was precipitated and was filtered and washed with 500 ml DM water and dried under vacuum at below 45° C. Yield: 21 gm.

Example 9—Process for Preparation of Form M of Apremilast

In a 500 ml round bottom flask, 100 ml acetone was charged followed by addition of 20 gm of apremilast and was heated at 45° C. to 50° C. to form clear solution. This clear solution was cooled. In another flask, water was cooled and above reaction solution was added. The slurry was formed. The resultant slurry was stirred for 7 to 10 hours at 10° C. to 15° C. The solid was filtered, washed with water and was dried for 10-15 hours. The product was yielded in 15 gm.

Example 10—Crystal Structure of Form M of Apremilast

Figures 17, 17A:
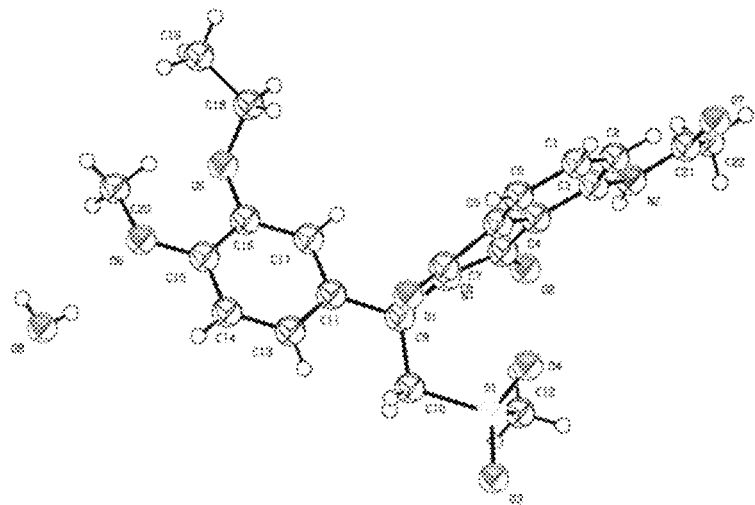
FIG. 17 depicts Crystal data of Form M of apremilast.
FIG. 17A depicts Oak Ridge Thermal Ellipsoid Plot (ORTEP) diagram of Form M of apremilast with 50% thermal ellipsoid.
Figure 17B:
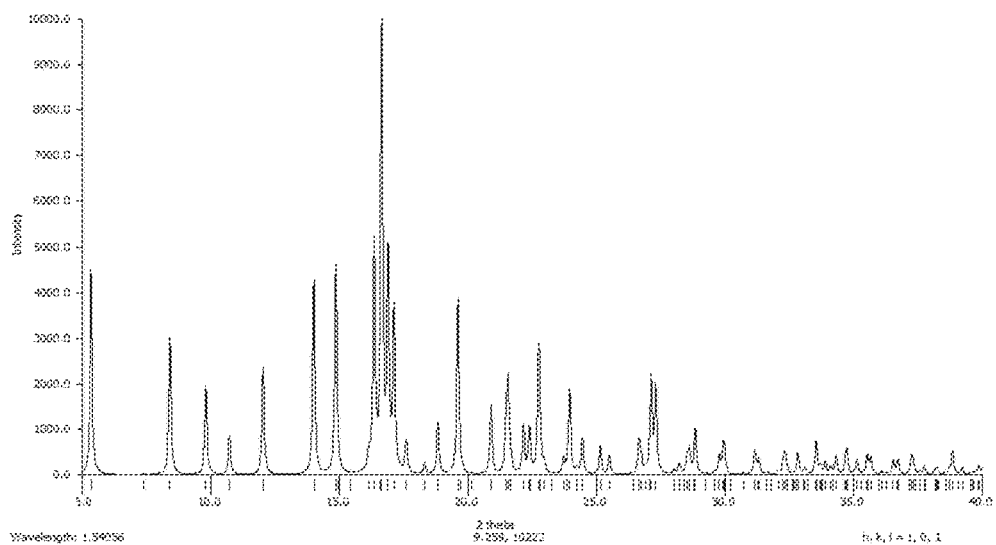
FIG. 17B depicts Rietveld plots of Form M of apremilast.
Figure 17C:
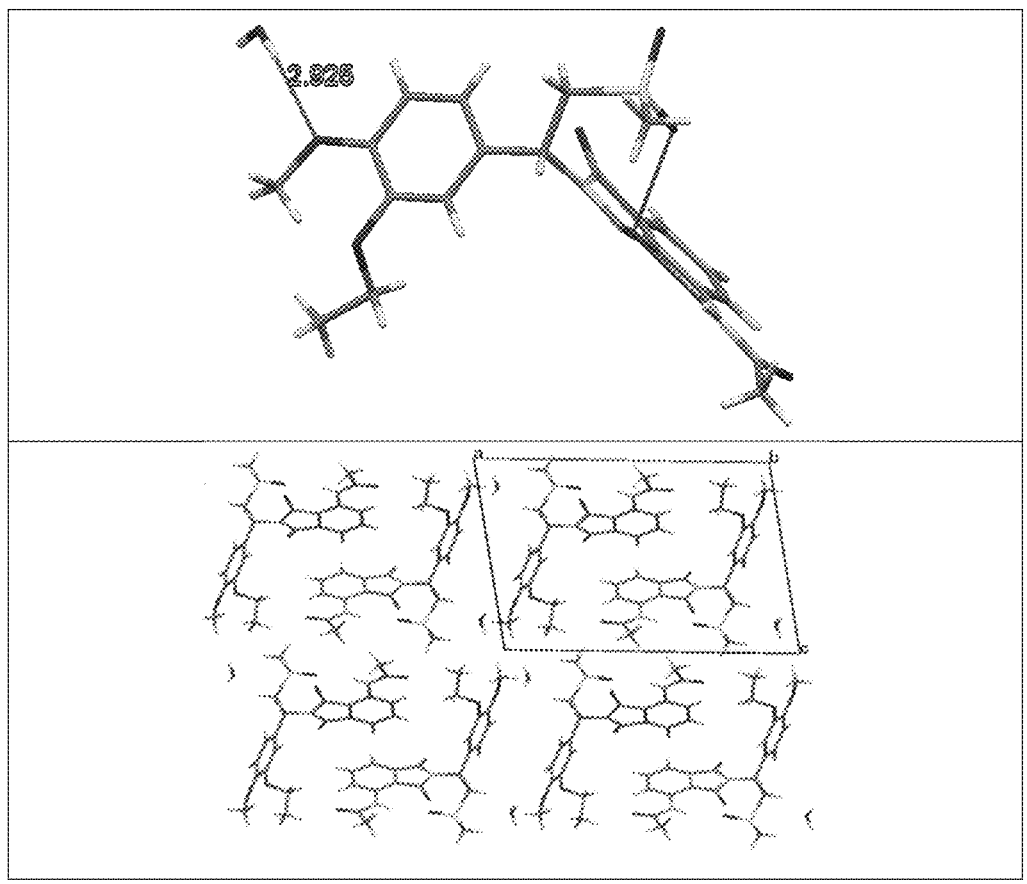
FIG. 17C depicts crystal structure of Form M of apremilast.

The crystal structure of Form M of apremilast was obtained from high resolution X-Ray diffraction patterns. The asymmetric unit was consisted of one unit of apremilast and one mole of water (FIG. 17A). The water molecules present in a discrete manner and hydrogen bonded to —OMe group of apremilast via auxiliary interactions (FIG. 17C).

The invention claimed is:
1. A crystalline Form M of apremilast having:
   i) a Powder X-Ray diffraction (PXRD) pattern substantially in accordance with FIG. 12;
   ii) a Powder X-Ray diffraction (PXRD) pattern having peaks at 5.3, 8.4, 9.8, 13.98, 14.85, 16.64, 19.59, 21.46, 27.23±0.2° 2theta value;
   iii) a Thermogravimetric analysis (TGA) substantially in accordance with FIG. 13, or
   iv) a differential scanning calorimetric (DSC) thermogram substantially in accordance with FIG. 14.
2. A process of preparing the crystalline Form M of apremilast of claim 1 comprising:
   a) contacting apremilast with at least one solvent;
   b) heating the mixture of step a);
   c) adding water to the mixture of step b);
   d) thereafter cooling the mixture; and
   e) isolating the Form M of apremilast.
3. The process of claim 2, wherein in step b), the mixture is heated to a temperature from about 30° C. to about 60° C.

4. The process of claim 2, wherein in step c), the mixture is cooled to a temperature of about 0° C. to about 20° C.

5. The process of claim 2, wherein the solvent is selected from the group consisting of acetone, tetrahydrofuran, and N,N-dimethylformamide; or mixture of at least two thereof.

6. A pharmaceutical composition comprising the crystalline Form M of apremilast of claim 1 and one or more pharmaceutically acceptable excipients.

7. The crystalline Form M of Apremilast of claim 1, having a moisture content between 1% to 5%.

8. The crystalline Form M of Apremilast of claim 1, having:
   i) a Powder X-Ray diffraction (PXRD) pattern substantially in accordance with FIG. 12;
   ii) a Powder X-Ray diffraction (PXRD) pattern having peaks at 5.3, 8.4, 9.8, 13.98, 14.85, 16.64, 19.59, 21.46, 27.23±0.2° 2theta value;
   iii) a Thermogravimetric analysis (TGA) substantially in accordance with FIG. 13, and
   iv) a differential scanning calorimetric (DSC) thermogram substantially in accordance with FIG. 14.

9. The crystalline Form M of Apremilast of claim 1, having:
   i) a Powder X-Ray diffraction (PXRD) pattern substantially in accordance with FIG. 12;
   iii) a Thermogravimetric analysis (TGA) substantially in accordance with FIG. 13, and
   iv) a differential scanning calorimetric (DSC) thermogram substantially in accordance with FIG. 14.

10. The crystalline Form M of Apremilast of claim 1, having:
    ii) a Powder X-Ray diffraction (PXRD) pattern having peaks at 5.3, 8.4, 9.8, 13.98, 14.85, 16.64, 19.59, 21.46, 27.23±0.2° 2theta value;
    iii) a Thermogravimetric analysis (TGA) substantially in accordance with FIG. 13, and
    iv) a differential scanning calorimetric (DSC) thermogram substantially in accordance with FIG. 14.

11. The crystalline Form M of Apremilast of claim 1, having:
    iii) a Thermogravimetric analysis (TGA) substantially in accordance with FIG. 13, and
    iv) a differential scanning calorimetric (DSC) thermogram substantially in accordance with FIG. 14.

12. The crystalline Form M of Apremilast of claim 1, having:
    ii) a Powder X-Ray diffraction (PXRD) pattern having peaks at 5.3, 8.4, 9.8, 13.98, 14.85, 16.64, 19.59, 21.46, 27.23±0.2° 2theta value.

* * * * *